United States Patent
Zhu

(10) Patent No.: US 9,827,422 B2
(45) Date of Patent: Nov. 28, 2017

(54) NEUROMODULATION USING STOCHASTICALLY-MODULATED STIMULATION PARAMETERS

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/146,145

(22) Filed: May 4, 2016

(65) Prior Publication Data

US 2016/0346546 A1    Dec. 1, 2016

Related U.S. Application Data

(60) Provisional application No. 62/167,630, filed on May 28, 2015.

(51) Int. Cl.
  *A61N 1/00* (2006.01)
  *A61N 1/36* (2006.01)
  *A61N 1/372* (2006.01)

(52) U.S. Cl.
  CPC ..... *A61N 1/36071* (2013.01); *A61N 1/36189* (2013.01); *A61N 1/37247* (2013.01)

(58) Field of Classification Search
  CPC .................. A61N 1/36071; A61N 1/36189
  USPC .................................................. 607/2, 45, 46
  See application file for complete search history.

(56) References Cited

U.S. PATENT DOCUMENTS

| | | |
|---|---|---|
| 4,338,945 A | 7/1982 | Kosugi et al. |
| 5,782,874 A | 7/1998 | Loos |
| 5,938,690 A | 8/1999 | Law et al. |
| 5,941,906 A | 8/1999 | Barreras, Sr. et al. |
| 6,246,912 B1 | 6/2001 | Sluijter et al. |
| 6,516,227 B1 | 2/2003 | Meadows et al. |
| 6,675,046 B2 | 1/2004 | Holsheimer |

(Continued)

FOREIGN PATENT DOCUMENTS

| | | |
|---|---|---|
| CN | 201139869 Y | 10/2008 |
| WO | WO-2006029257 A2 | 3/2006 |

(Continued)

OTHER PUBLICATIONS

"U.S. Appl. No. 14/195,632, Non Final Office Action dated Mar. 18, 2015", 6 pgs.

(Continued)

*Primary Examiner* — Nadia A Mahmood
(74) *Attorney, Agent, or Firm* — Schwegman Lundberg & Woessner, P.A.

(57) ABSTRACT

An example of a system may include an electrode arrangement and a neuromodulation device configured to use electrodes in the electrode arrangement to generate a neuromodulation field. The neuromodulation device may include a neuromodulation generator, a neuromodulation control circuit and a storage. The storage may include a stochastically-modulated neuromodulation parameter set and the stochastically-modulated neuromodulation parameter set may include at least one stochastically-modulated parameter. The controller may be configured to control the neuromodulation generator using the stochastically-modulation parameter set to generate the neuromodulation field.

20 Claims, 7 Drawing Sheets

(56) References Cited

U.S. PATENT DOCUMENTS

| | | |
|---|---|---|
| 6,895,280 B2 | 5/2005 | Meadows et al. |
| 6,993,384 B2 | 1/2006 | Bradley et al. |
| 7,076,307 B2 | 7/2006 | Boveja et al. |
| 7,317,948 B1 | 1/2008 | King et al. |
| 7,333,857 B2 | 2/2008 | Campbell |
| 7,539,538 B2 | 5/2009 | Parramon et al. |
| 7,627,384 B2 | 12/2009 | Ayal et al. |
| 7,650,184 B2 | 1/2010 | Walter |
| 7,979,133 B2 | 7/2011 | Feler et al. |
| 7,987,000 B2 | 7/2011 | Moffitt et al. |
| 8,010,198 B2 | 8/2011 | Libbus et al. |
| 8,019,439 B2 | 9/2011 | Kuzma et al. |
| 8,036,754 B2 | 10/2011 | Lee et al. |
| 8,160,328 B2 | 4/2012 | Goetz et al. |
| 8,175,705 B2 | 5/2012 | Libbus |
| 8,180,129 B2 | 5/2012 | Goetz et al. |
| 8,224,453 B2 | 7/2012 | De Ridder |
| 8,249,711 B2 | 8/2012 | Libbus et al. |
| 8,255,057 B2 | 8/2012 | Fang et al. |
| 8,355,797 B2 | 1/2013 | Caparso et al. |
| 8,380,318 B2 | 2/2013 | Kishawi et al. |
| 8,401,653 B2 | 3/2013 | Libbus et al. |
| 8,412,345 B2 | 4/2013 | Moffitt |
| 8,437,857 B2 | 5/2013 | Moffitt et al. |
| 8,455,716 B2 | 6/2013 | Huang et al. |
| 8,504,147 B2 | 8/2013 | Deem et al. |
| 8,594,785 B2 | 11/2013 | Bradely |
| 8,615,300 B2 | 12/2013 | Feler et al. |
| 8,644,947 B2 | 2/2014 | Zhu et al. |
| 8,649,874 B2 | 2/2014 | Alataris et al. |
| 8,660,653 B2 | 2/2014 | Kothandaraman |
| 8,670,831 B2 | 3/2014 | Wacnik et al. |
| 8,676,329 B2 | 3/2014 | Wacnik et al. |
| 8,676,331 B2 | 3/2014 | Parker |
| 8,694,104 B2 | 4/2014 | Libbus et al. |
| 8,700,178 B2 | 4/2014 | Anderson |
| 8,706,250 B2 | 4/2014 | Zhu et al. |
| 8,731,675 B2 | 5/2014 | Ranu et al. |
| 8,751,009 B2 | 6/2014 | Wacnik |
| 8,788,048 B2 | 7/2014 | Bennett et al. |
| 8,788,054 B2 | 7/2014 | Kothandaraman et al. |
| 8,909,350 B2 | 12/2014 | Lee |
| 9,138,582 B2 | 9/2015 | Doan |
| 9,174,053 B2 | 11/2015 | Zhu |
| 9,238,138 B2 | 1/2016 | Lee et al. |
| 2002/0143365 A1 | 10/2002 | Herbst |
| 2003/0139781 A1 | 7/2003 | Bradley et al. |
| 2004/0116978 A1 | 6/2004 | Bradley |
| 2004/0267333 A1 | 12/2004 | Kronberg |
| 2005/0060008 A1 | 3/2005 | Goetz |
| 2005/0267546 A1 | 12/2005 | Parramon et al. |
| 2006/0015153 A1 | 1/2006 | Gliner et al. |
| 2006/0149337 A1 | 7/2006 | John |
| 2007/0027486 A1* | 2/2007 | Armstrong ......... A61N 1/36071 607/2 |
| 2007/0142874 A1 | 6/2007 | John |
| 2007/0150036 A1 | 6/2007 | Anderson |
| 2007/0167991 A1 | 7/2007 | DiLorenzo |
| 2007/0213783 A1 | 9/2007 | Pless |
| 2008/0077192 A1 | 3/2008 | Harry et al. |
| 2008/0188909 A1 | 8/2008 | Bradley |
| 2008/0243204 A1 | 10/2008 | Uthman et al. |
| 2009/0024189 A1 | 1/2009 | Lee et al. |
| 2009/0118777 A1 | 5/2009 | Iki et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2010/0010566 A1 | 1/2010 | Thacker et al. |
| 2010/0023090 A1 | 1/2010 | Jaax et al. |
| 2010/0121409 A1 | 5/2010 | Kothandaraman et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0009923 A1 | 1/2011 | Lee |
| 2011/0213440 A1 | 9/2011 | Fowler et al. |
| 2011/0213442 A1 | 9/2011 | Pless |
| 2011/0282414 A1 | 11/2011 | Kothandaraman et al. |
| 2011/0295332 A1 | 12/2011 | Osorio |
| 2012/0059446 A1 | 3/2012 | Wallace et al. |
| 2012/0083709 A1 | 4/2012 | Parker et al. |
| 2012/0101547 A1 | 4/2012 | Jensen et al. |
| 2012/0197336 A1 | 8/2012 | Su |
| 2012/0215279 A1 | 8/2012 | Libbus |
| 2012/0253422 A1 | 10/2012 | Thacker et al. |
| 2012/0265279 A1 | 10/2012 | Zhu |
| 2012/0283797 A1 | 11/2012 | De Ridder |
| 2012/0290041 A1 | 11/2012 | Kim et al. |
| 2012/0296395 A1 | 11/2012 | Hamann et al. |
| 2013/0018437 A1 | 1/2013 | De Ridder |
| 2013/0066411 A1 | 3/2013 | Thacker et al. |
| 2013/0116752 A1 | 5/2013 | Parker et al. |
| 2013/0131760 A1 | 5/2013 | Rao et al. |
| 2013/0268021 A1 | 10/2013 | Moffitt |
| 2013/0296975 A1 | 11/2013 | Lee et al. |
| 2013/0304152 A1 | 11/2013 | Bradley et al. |
| 2014/0046407 A1 | 2/2014 | Ben-Ezra et al. |
| 2014/0081349 A1 | 3/2014 | Lee et al. |
| 2014/0088674 A1 | 3/2014 | Bradley |
| 2014/0213926 A1 | 7/2014 | Vaidyanathan |
| 2014/0222100 A1 | 8/2014 | Libbus et al. |
| 2014/0222113 A1 | 8/2014 | Gliner et al. |
| 2014/0243925 A1 | 8/2014 | Kothandaraman |
| 2014/0257428 A1 | 9/2014 | Zhu |
| 2014/0277267 A1 | 9/2014 | Vansickle et al. |
| 2014/0364920 A1 | 12/2014 | Doan et al. |
| 2014/0364921 A1 | 12/2014 | Legay et al. |
| 2015/0217117 A1 | 8/2015 | Hershey |
| 2016/0001087 A1 | 1/2016 | Moffitt |
| 2016/0106985 A1 | 4/2016 | Zhu |
| 2016/0129247 A1 | 5/2016 | Lee et al. |
| 2016/0279422 A1 | 9/2016 | Libbus et al. |

FOREIGN PATENT DOCUMENTS

| | | |
|---|---|---|
| WO | WO-2006135791 A2 | 12/2006 |
| WO | WO-2015119768 A1 | 8/2015 |
| WO | WO-2016191055 A1 | 12/2016 |

OTHER PUBLICATIONS

"U.S. Appl. No. 14/195,632, Notice of Allowance dated Jun. 26, 2015", 5 pgs.

"U.S. Appl. No. 14/195,632, Response filed Jun. 18, 2015 to Non Final Offfice Action dated Mar. 18, 2015", 10 pgs.

"U.S. Appl. No. 14/600,649, Non Final Office Action dated Oct. 1, 2015", 12 pgs.

"U.S. Appl. No. 14/600,649, Notice of Allowance dated Mar. 7, 2016", 8 pgs.

"U.S. Appl. No. 14/600,649, Response filed Jan. 4, 2016 to Non Final Office Action dated Oct. 1, 2015", 8 pgs.

"U.S. Appl. No. 14/920,229, Non Final Office Action dated May 3, 2016", 8 pgs.

"U.S. Appl. No. 14/920,229, Preliminary Amendment filed Jan. 13, 2016", 7 pgs.

"International Application Serial No. PCT/US2015/012030, International Search Report dated Apr. 21, 2015", 5 pgs.

"International Application Serial No. PCT/US2015/012030, Written Opinion dated Apr. 21, 2015", 7 pgs.

Warman, Eduardo N., et al., "Modeling the Effects of Electric Fields on Nerve Fibers: Determination of Excitation Thresholds", IEEE Transactions on Biomedical Engineering, vol. 39, No. 12, Dec. 1992, (Dec. 1992).

"International Application Serial No. PCT/US2016/030686, International Search Report dated Jul. 25, 2016", 4 pgs.

(56) References Cited

OTHER PUBLICATIONS

"International Application Serial No. PCT/US2016/030686, Written Opinion dated Jul. 25, 2016", 6 pgs.

* cited by examiner

NEUROMODULATION USING STOCHASTICALLY-MODULATED STIMULATION PARAMETERS

CLAIM OF PRIORITY

This application claims the benefit of priority under 35 U.S.C. §119(e) of U.S. Provisional Patent Application Ser. No. 62/167,630, filed on May 28, 2015, which is herein incorporated by reference in its entirety.

TECHNICAL FIELD

This document relates generally to medical devices, and more particularly, to systems, devices and methods for delivering neural modulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

SUMMARY

An example (e.g. "Example 1") of subject matter (e.g. a system) may include an electrode arrangement and a neuromodulation device configured to use electrodes in the electrode arrangement to generate a neuromodulation field. The neuromodulation device may include a neuromodulation generator, a neuromodulation control circuit and a storage. The storage may include a stochastically-modulated neuromodulation parameter set and the stochastically-modulated neuromodulation parameter set may include at least one stochastically-modulated parameter. The controller may be configured to control the neuromodulation generator using the stochastically-modulation parameter set to generate the neuromodulation field.

In Example 2, the subject matter of Example 1 may optionally be configured such that the system further includes a stochastic modulator configured to stochastically modulate at least one parameter of a neuromodulation parameter set to provide the at least one stochastically-modulated parameter in the stochastically-modulated neuromodulation parameter set.

In Example 3, the subject matter of Example 2 may optionally be configured such that the neuromodulation device includes the stochastic modulator.

In Example 4, the subject matter of Example 2 may optionally be configured such that the system includes a programming device. The programming device may include the stochastic modulator and is configured to program the stochastically-modulated neuromodulation parameter set into the neuromodulation device.

In Example 5, the subject matter of any one or any combination of Examples 2-4 may optionally be configured such that the stochastic modulator is programmed with at least one modulation model, and is configured to use the at least one modulation model to stochastically modulate the at least one parameter to provide the at least one stochastically-modulated parameter. The at least one modulation model may include a probabilistic distribution model, or a stochastic process model, or a real-time/semi-real-time computational model.

In Example 6, the subject matter of Example 5 may optionally be configured such that the stochastic modulator is programmed with another modulation model and is configured to use the other modulation model to stochastically modulate another parameter.

In Example 7, the subject matter of any one or any combination of Examples 5-6 may optionally be configured such that the stochastic modulator is configured to use a random or pseudo-random samples of the modulation model to stochastically modulate the at least one parameter.

In Example 8, the subject matter of Example 7 may optionally be configured such that the stochastic modulator includes a timer or counter configured to control when the stochastic modulator advances from one sample to another sample.

In Example 9, the subject matter of Example 7 may optionally be configured such that the stochastic modulator includes stochastic process rules used to identify if a subsequent sample is permissible for a sequence of random or pseudo-random samples used to stochastically modulate the at least one parameter.

In Example 10, the subject matter of any one or any combination of Examples 1-9 may optionally be configured such that the system further includes a user interface configured for use to program the stochastic modulator.

In Example 11, the subject matter of Example 10 may optionally be configured such that the user interface is configured to allow a user to select a modulation model to be used by the stochastic modulator.

In Example 12, the subject matter of any one or any combination of Examples 10-11 may optionally be configured such that the user interface is configured to allow a user to select a parameter to be stochastically-modulated using the stochastic modulator.

In Example 13, the subject matter of any one or any combination of Examples 10-12 may optionally be configured such that the user interface is configured to allow a user to select at least one of the following: at least one model parameter for a stochastic modulation model, the at least one model parameter to at least partially define or constrain the stochastic modulation model; sampling rules to create random or pseudo-random samples of the stochastic modulation model; rules to control when the stochastic modulator advances from one sample to another sample; or rules used to identify if a subsequent sample is permissible for a sequence of random or pseudo-random samples to provide a stochastic process.

In Example 14, the subject matter of any one or any combination of Examples 1-13 may optionally be configured such that the at least one stochastically-modulated parameter includes a temporal modulation parameter.

In Example 15, the subject matter of any one or any combination of Examples 1-14 may optionally be configured such that the at least one stochastically-modulated parameter includes a spatial parameter.

An example (e.g. "Example 16") of subject matter (e.g. a system) may include an electrode arrangement and a neuromodulation device configured to use electrodes in the electrode arrangement to generate a neuromodulation field. The neuromodulation device may include a neuromodulation generator, a neuromodulation control circuit and a storage. The storage may include a stochastically-modulated neuromodulation parameter set, the stochastically-modulated neuromodulation parameter set including at least one stochastically-modulated parameter. The controller may be configured to control the neuromodulation generator using the stochastically-modulation parameter set to generate the neuromodulation field.

In Example 17, the subject matter of Example 16 may optionally be configured such that the system further includes a stochastic modulator configured to stochastically modulate at least one parameter of a neuromodulation parameter set to provide the at least one stochastically-modulated parameter in the stochastically-modulated neuromodulation parameter set.

In Example 18, the subject matter of Example 17 may optionally be configured such that the neuromodulation device includes the stochastic modulator.

In Example 19, the subject matter of Example 17 may optionally be configured such that the system includes a programming device. The programming device may include the stochastic modulator and may be configured to program the stochastically-modulated neuromodulation parameter set into the neuromodulation device.

In Example 20, the subject matter of Example 17 may optionally be configured such that the stochastic modulator is programmed with at least one modulation model, and is configured to use the at least one modulation model to stochastically modulate the at least one parameter to provide the at least one stochastically-modulated parameter. The at least one modulation model includes a probabilistic distribution model, or a stochastic process model, or a real-time/semi-real-time computational model.

In Example 21, the subject matter of Example 20 may optionally be configured such that the stochastic modulator is programmed with another modulation model, and is configured to use the other modulation model to stochastically modulate another parameter.

In Example 22, the subject matter of Example 20 may optionally be configured such that the stochastic modulator is configured to use a random or pseudo-random samples of the modulation model to stochastically modulate the at least one parameter.

In Example 23, the subject matter of Example 22 may optionally be configured such that the stochastic modulator includes a timer or counter configured to control when the stochastic modulator advances from one sample to another sample.

In Example 24, the subject matter of Example 22 may optionally be configured such that the stochastic modulator includes stochastic process rules used to identify if a subsequent sample is permissible for a sequence of random or pseudo-random samples used to stochastically modulate the at least one parameter.

In Example 25, the subject matter of Example 1 may optionally be configured such that the system further includes a user interface configured for use to program the stochastic modulator.

In Example 26, the subject matter of Example 25 may optionally be configured such that the user interface is configured to allow a user to select a modulation model to be used by the stochastic modulator.

In Example 27 the subject matter of Example 25 may optionally be configured such that the user interface is configured to allow a user to select a parameter to be stochastically-modulated using the stochastic modulator.

In Example 28, the subject matter of Example 25 may optionally be configured such that the user interface is configured to allow a user to select at least one of the following: at least one model parameter for a stochastic modulation model, the at least one model parameter to at least partially define or constrain the stochastic modulation model; sampling rules to create random or pseudo-random samples of the stochastic modulation model; rules to control when the stochastic modulator advances from one sample to another sample; or rules used to identify if a subsequent sample is permissible for a sequence of random or pseudo-random samples to provide a stochastic process.

In Example 29, the subject matter of Example 16 may optionally be configured such that the at least one stochastically-modulated parameter includes a temporal modulation parameter.

In Example 30, the subject matter of Example 16 may optionally be configured such that the at least one stochastically-modulated parameter includes a spatial parameter.

An example (e.g. "Example 31") of subject matter (e.g. a method for delivering neuromodulation, a means for performing acts, or a machine-readable medium including instructions that, when performed by the machine, cause the machine to perform acts), may include stochastically modulating at least one neuromodulation parameter to provide a stochastically-modulated neuromodulation parameter set, and generating a neuromodulation field using the stochastically-modulated neuromodulation parameter set.

In Example 32, the subject matter of Example 31 may optionally be configured such that the method may further include using a modulation model to stochastically modulate the at least one parameter to provide the at least one stochastically-modulated parameter. The modulation model may include a probabilistic distribution model, or a stochastic process model, or a real-time/semi-real-time computational model.

In Example 33, the subject matter of Example 31 may optionally be configured such that the method may further include using another modulation model to stochastically-modulate at least one other parameter.

In Example 34, the subject matter of Example 31 may optionally be configured such that the method may further include implementing stochastic process rules to enforce a permissible sequence of random or pseudo-random samples of a probabilistic distribution used to stochastically modulate the at least one parameter.

In Example 35, the subject matter of Example 31 may optionally be configured such that stochastically modulating at least one neuromodulation parameter may include stochastically modulating at least one temporal parameter or stochastically modulating at least one spatial parameter.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
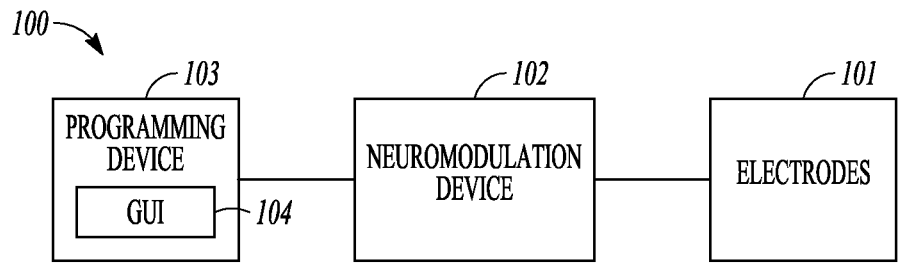
FIG. 1 illustrates an embodiment of a neuromodulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A stochastic system is non-deterministic or random, having random probability distribution that can be statistically analyzed. The activity of neurons in the central nervous system appears noisy, as their firing times are random when they are firing at a given mean rate. As such, many aspects of brain function involve central neural processing that has a random or stochastic property. For example, probabilistic decision making, perception, memory recall, short-term memory, attention, and even creativity have a stochastic property. In many of these processes, the noise caused by the random neural firing times can be useful. By way of example, the noise may provide stochastic resonance, where the resonance between a weak signal and background noise allows the weak signal to become detectable. In addition, several forms of neural adaptive behaviors or neuroplasticity can occur as a result of constant invariant stimulation, such as neural adaptation, habituation, stimulus generalization, etc., causing reduced sensitivity to the stimulus.

Various embodiments of the present subject matter stochastically modulate neuromodulation parameters to introduce variation into the modulation by dynamically varying the modulation within a therapeutic window, making it complementary to tonic (time invariant) neuromodulation. There may be benefits using stochastically-modulated stimulation parameters in neuromodulation. By way of example, benefits may include comfort perception of stimulation, increased therapeutic effect, reduced side effect, and improved long term efficacy (therapeutic longevity).

The neuromodulation parameters that may be stochastically-modulated may include, but are not limited to, one or more of pulse amplitude, pulse width, pulse rate, pulse delay, inter-pulse interval, hold off, number of burst, duty cycle, and on and off of multiple stimulation settings. Neuromodulation parameters may be stochastically-modulated to provide temporal variation of the modulation field, to provide spatial variation of the modulation field, or to provide both temporal and spatial variation of the modulation field. Modulating a parameter involves changing a value of the parameter over time.

A stochastic modulation model may be at least partially defined or constrained by model parameter(s). By way of example and not limitation, a stochastic modulation model may include a probabilistic distribution. Probabilistic distributions may be at least partially defined by distribution factors which may function as model parameters for the stochastic modulation model. For example, mean and standard deviation are distribution factors of a Gaussian distribution. Modulation parameter(s) may be selected to control characteristics of the stochastic modulation model. For example, various embodiments may apply a probabilistic model to distribute stimulation parameters with a mean value, which may be selected by a user, so that the stimulation parameter can be randomly varied within a therapeutic window while maintaining the mean value. For example, if the parameter to be stochastically-modulated is frequency, the user can also select the mean value for the frequency to control the average therapeutic dose delivered to the targeted neural tissue. A relatively smaller standard deviation provides more randomized or pseudo-randomized samples that are closer to the mean, and a relatively large standard deviation provides more randomized or pseudo-randomized samples that are further away from the mean. Some embodiments may allow the user to enter value(s) (e.g. a sigma value) to prohibit the extremes in the distribution, or to specify the depth of variation. A value of 2 sigma, by way of example, may be used prohibit about the lowest 2% and the highest 2% in the normal distribution from being used to stochastically modulate the neuromodulation parameter (or allow about the 95% in the middle of the normal distribution to stochastically modulate the neuromodulation parameter). In various embodiments, the model parameter(s) that can be entered or selected by the user may also include sigma values or other values to restrict the permissible range of random values in the stochastic modulation model.

Various embodiments may apply a stochastic modulation model to create spatial variance in stimulation, e.g.: selection (or on/off) of stimulation electrodes, specify polarity (or cathode/anode) of stimulation electrodes, selection (or on/off) of stimulation areas/channels. Spatial variation may be combined with temporal variation. The therapeutic stimulation may be embedded in a background "noise" stimulation which may provide stochastic resonance.

Various embodiments may implement stochastically-modulated neuromodulation parameters for deep brain stimulation. Various embodiments may implement stochastically-modulated neuromodulation parameters for spinal cord stimulation. Various embodiments may implement stochastically-modulated neuromodulation parameters for functional modulation such as may be implemented for physical therapy or to improve sensory, motor, or cognitive function. Stochastically-modulated neuromodulation may be delivered to other neural tissue for other therapy. Non-exhaustive examples of other neuromodulation that may be stochastically-modulated include cortex stimulation, transcranial stimulation, peripheral nerve stimulation, and peripheral nerve field stimulation.

A stochastic model may use any of a number of stochastical distributions. The stochastical distributions may be currently known, or may be developed as a model for activity in a targeted neural tissue. Stochastical distributions may be a continuous probabilistic distribution or a discrete probabilistic distribution. Examples of continuous probabilistic distributions include a continuous uniform distribution, a Gaussian/Normal distribution, and Poisson (Poisson distribution, exponential distribution, gamma distribution). Examples of discrete probabilistic distributions include a discrete uniform distribution, binomial distribution (e.g. flipping a coin, rolling a die), Poisson, and Bernoulli.

These stochastical distributions may be used to create a pool of sample values. A random or pseudo random selection of these sample values may provide a sequence of values used to modulate at least one parameter in the neuromodulation parameter set. Furthermore, there may be rules set up to enforce a stochastical process, which represents a sequence of random variables and the time series associated with these random variables. By way of example, a subsequent sample taken from a randomized selection may only be used if it follows the previous sample within the bounds of the rule(s). By way of example and not limitation, the rules may prevent a sequence of randomized values where the difference in values for successive samples is too large. These rules may be developed based on observed neural activity in the targeted neural tissue.

Various embodiments may stochastically modulate the neuromodulation parameter(s) using a continuous probabilistic distribution such as uniform or Gaussian distributions. Various embodiments may stochastically modulate the neuromodulation parameter(s) to provide a spatial distribution of the stimulation location using a discrete probabilistic distribution such as a discrete uniform distribution. Various embodiments control the train of neuromodulation pulses to follow a discrete process such as, but not limited to, a Poission process.

Stochastic modulation of a neuromodulation parameter is distinguishable from spectrally distributed random variables, for instance, white noise, and pink noise. White noise is a random signal or process that has an equal power spectral density across the frequency. In a discrete form, the white noise is a collection or a sequence of uncorrelated/independent samples with zero mean and finite variance. Pink noise is a random signal or process with power spectral density inversely proportional to the frequency. In contrast, stochastical modulation of one or more neuromodulation parameters will typically not provide a zero mean. Furthermore, a stochastic process describes the evolution of random variables over time, which means the samples may be correlated.

FIG. 1 illustrates an embodiment of a neuromodulation system. The illustrated system 100 includes electrodes 101, a neuromodulation device 102, and a programming device 103. The electrodes 103 are configured to be placed on or near one or more neural targets in a patient. The electrodes 101 may form part of an electrode arrangement. The neuromodulation device 102 may be an implantable medical device operable when implanted within a patient. The neuromodulation device 102 may be an external device operable external to the patient. The neuromodulation device 102 is configured to be electrically connected to electrodes 101 and deliver neuromodulation energy, such as in the form of electrical pulses, to the one or more neural targets though electrodes 101. The delivery of the neuromodulation is controlled using a plurality of neuromodulation parameters, such as neuromodulation parameters specifying the electrical pulses and a selection of electrodes through which each of the electrical pulses is delivered. In various embodiments, at least some parameters of the plurality of neuromodulation parameters are programmable by a user, such as a physician or other caregiver. The programming device 103 may provide the user with accessibility to the user-programmable parameters. In various embodiments, the programming device 103 is configured to be communicatively coupled to neuromodulation device via a wired or wireless link. In various embodiments, the programming device 103 includes a graphical user interface (GUI) 104 that allows the user to set and/or adjust values of the user-programmable neuromodulation parameters.

Figure 2:
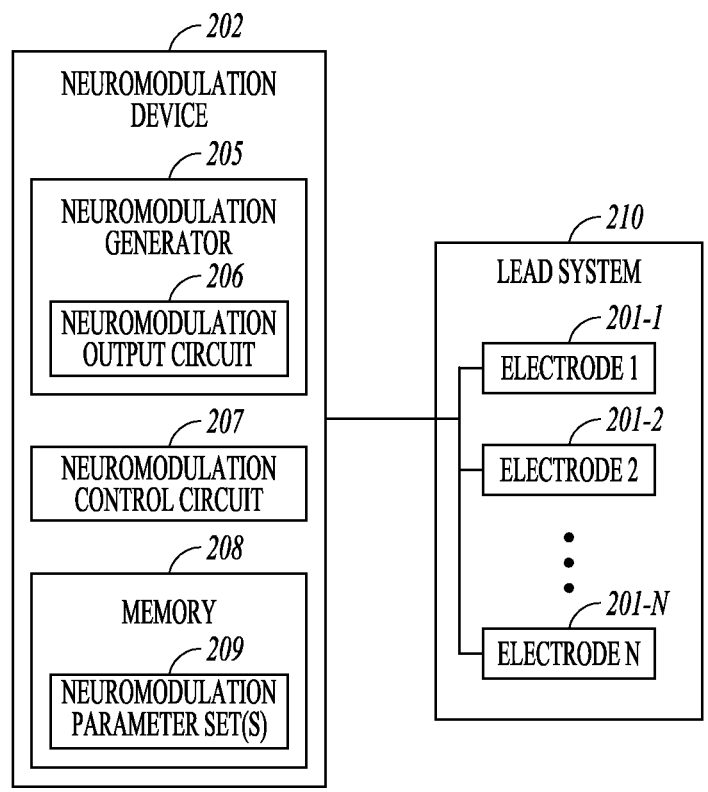
FIG. 2 illustrates an embodiment of a neuromodulation device connected to a lead system, such as may be implemented in the neuromodulation system of FIG. 1.

FIG. 2 illustrates an embodiment of a neuromodulation device 202 connected to a lead system 210, such as may be implemented in the neuromodulation system 100 of FIG. 1. The illustrated embodiment of the neuromodulation device 202 includes a neuromodulation generator 205 with a neuromodulation output circuit 206, a neuromodulation control circuit 207, and memory 208 with neuromodulation parameter set(s) 209. Those of ordinary skill in the art will understand that the neuromodulation system 202 may include additional components such as sensing circuitry for patient monitoring and/or feedback control of the therapy, telemetry circuitry and power. The neuromodulation generator 205 with the neuromodulation output circuit 206 produces and delivers neuromodulation pulses. The neuro modulation control circuit 207 controls the delivery of the neuromodulation pulses using neuromodulation parameters in a neuromodulation parameter set. The lead system 210 may include one or more leads each configured to be electrically connected to neuromodulation device 202 and a plurality of electrodes 201-1 to 201-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between the neuromodulation output circuit 206 and tissue of the patient. The neuromodulation pulses are each delivered from the neuromodulation output circuit 206 through a set of electrodes selected from the electrodes 201-1 to 202-N. The number of leads and the number of electrodes on each lead may depend on, for example, the distribution of target(s) of the neuromodulation and the need for controlling the distribution of electric field at each target. By way of example and not limitation, the lead system may include two leads each having eight electrodes.

The neuromodulation system may be configured to modulate spinal target tissue, brain tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow more desirable modulation parameters to be determined based on patient feedback or other means and to subsequently program the desired modulation parameter sets.

Conventional SCS therapy is discussed herein as an example. The present subject matter, however, is not limited to conventional SCS therapy, as it may also be implemented to stochastically modulate neuromodulation parameters used in sub-perception SCS or deep brain stimulation or vagal stimulation or stimulation of other neural targets.

Conventional programming for SCS therapy uses paresthesia to select an appropriate modulation parameter set. The paresthesia induced by the modulation and perceived by the patient should be located in approximately the same place in the patient's body as the pain that is the target of treatment. When leads are implanted within the patient, an operating room (OR) mapping procedure may be performed to apply electrical modulation to test placement of the leads and/or electrodes, thereby assuring that the leads and/or electrodes are implanted in effective locations within the patient.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array.

Figure 3:
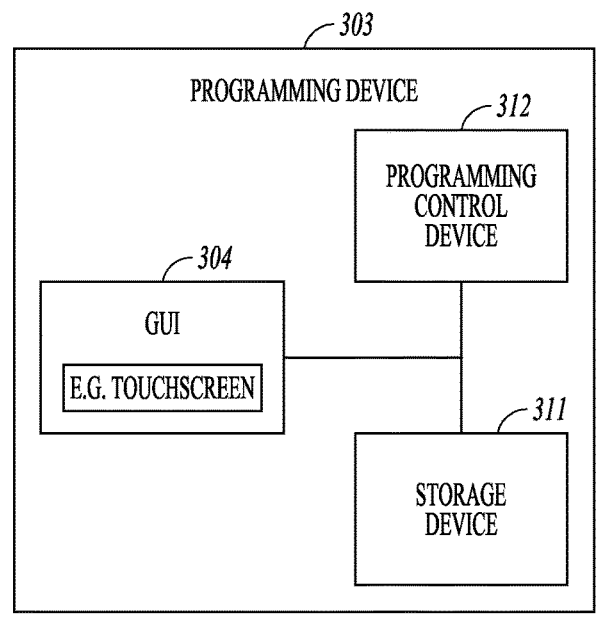
FIG. 3 illustrates an embodiment of a programming device, such as may be used in the neuromodulation system of FIG. 1.

FIG. 3 illustrates an embodiment of a programming device 303, such as may be used in the neuromodulation system of FIG. 1. The programming device 303 may include a memory or storage device 311 which may be referred to as storage, a programming control circuit 312, and a GUI 304 such as a touchscreen. The programming control circuit 312 may be used to generate the plurality of neuromodulation parameters that controls the delivery of the neuromodulation pulses according to the pattern of the neuromodulation pulses. In various embodiments, the GUI 304 may include any type of presentation device, such as interactive or non-interactive screens, and any type of user input devices that allow the user to program the neuromodulation parameters, such as touchscreen, keyboard, keypad, touchpad, trackball, joystick, and mouse. The storage device 311 may store, among other things, neuromodulation parameters to be programmed into the neuromodulation device. The programming device 303 may transmit the plurality of neuromodulation parameters to the neuromodulation device. In some embodiments, the programming device 303 may transmit power to the neuromodulation device. The programming control circuit 312 may generate the plurality of neuromodulation parameters. In various embodiments, the programming control circuit 312 may check values of the plurality of neuromodulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
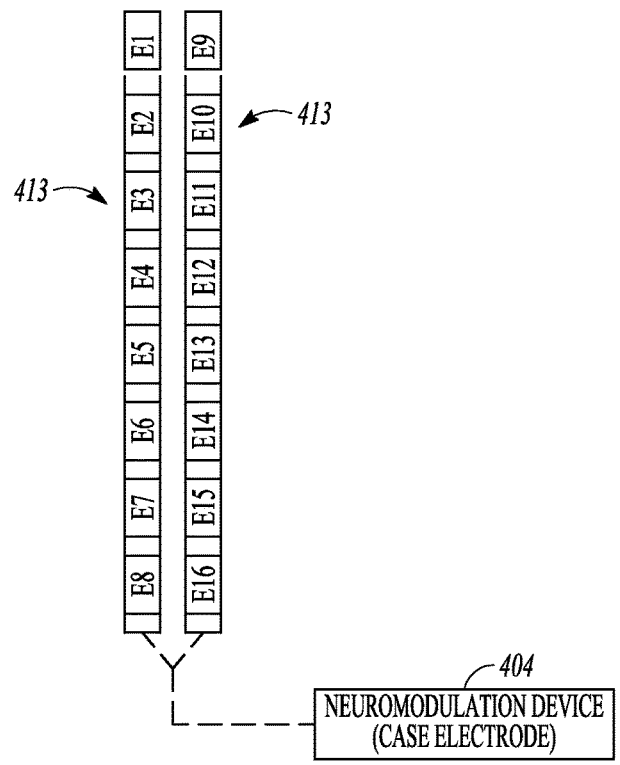
FIG. 4 illustrates, by way of example, some features of the neuromodulation leads and a neuromodulation device.

FIG. 4 illustrates, by way of example, some features of the neuromodulation leads 413 and a neuromodulation device 404. The neuromodulation device 404 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable device may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The implanted device may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the implanted device.

Electrical neuromodulation energy is provided to the electrodes in accordance with a set of neuromodulation parameters programmed into the neuromodulation device. The electrical modulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). The electrical pulse parameters may define an intermittent neuromodulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be a case electrode of the implanted device. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the neuromodulation device, so that neuromodulation energy is transmitted between the selected electrode and case.

Any of the electrodes (e.g. E1-E16 and the case electrode) may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels.

The neuromodulation device may be configured to individually control the magnitude of electrical current flowing through each of the electrodes, which may be referred to as multiple independent current control (MICC). For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. The neuromodulation device may be designed with mixed current and voltage regulated devices. The individual control of electrical current through each of the electrodes allows the neuromodulation device to fractionalize the current. The fractionalization across the electrical modulation lead can vary in any manner as long as the total of fractionalized currents equals 100%.

The SCS system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle. Various embodiments stochastically modulate values for one or more neuromodulation parameters such as these and others.

Some embodiments are configured to provide a neuromodulation parameter set to create a desired neuromodulation field shape (e.g. a broad and uniform neuromodulation field such as may be useful to prime targeted neural tissue with sub-perception modulation or a field shape to reduce or minimize modulation of non-targeted tissue. Various embodiments stochastically modulate values of one or more neuromodulation parameters associated with controlling the field shape in order to stochastically modulate the neuromodulation field shape.

Figure 5:
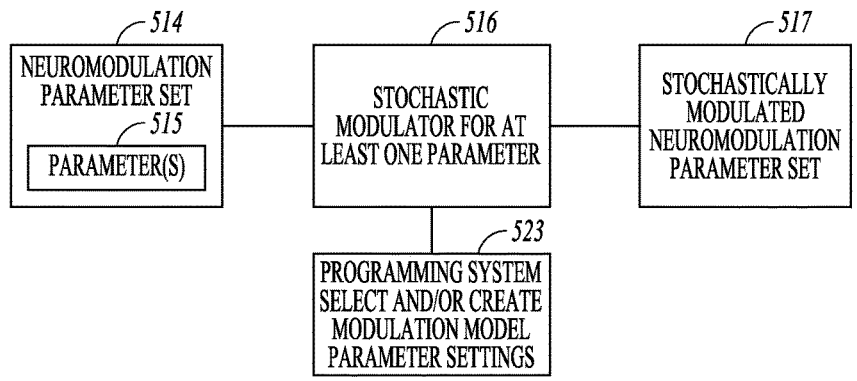
FIG. 5 illustrates, by way of example and not limitation, a system to stochastically modulate neuromodulation.

FIG. 5 illustrates, by way of example and not limitation, a system to stochastically modulate neuromodulation. The illustrated system may include at least one neuromodulation parameter set 514 that includes a plurality of parameters that may be used to define the neuromodulation pulse parameters (e.g. amplitude, pulse width, pulse frequency, on/off timing, timing channels, etc.) and electrode configuration(s) used in the neuromodulation. The at least one neuromodulation parameter set may include one or more neuromodulation parameters 515 selected to be stochastically-modulated by a stochastic modulator 516 to provide a stochastically-modulated neuromodulation parameter set 517. The stochastically-modulated neuromodulation parameter set 517 may be used to generate the stochastically-modulated neuromodulation field. In some embodiments, the stochastic modulator is programmable. Thus, the system illustrated in FIG. 5 may optionally include a programming system 523 which may be configured for use to select a modulation model(s), or to create modulation model(s), or to create and select modulation model(s). Additionally or alternatively, the programming system 523 may be configured for use to program parameter settings. The stochastic modulator may use modulation model(s) to stochastically-modulate the neuromodulation parameter(s). The modulation model(s) may include probabilistic distribution model(s), or stochastic process model(s), or real-time/semi-real-time computational model(s), or combinations of these different types of models.

Figure 6A:
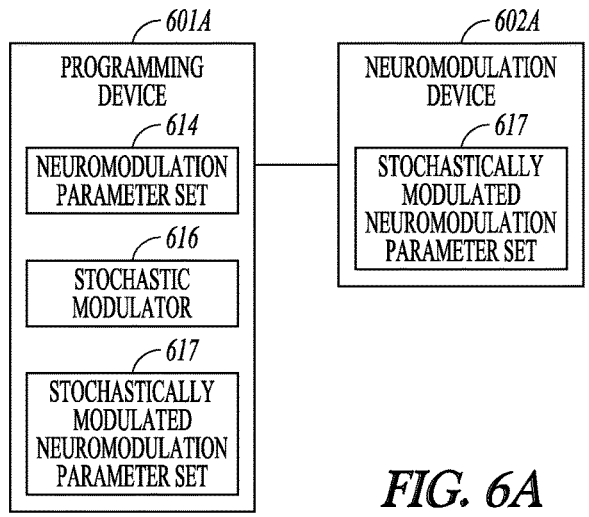
FIGS. 6A-6D illustrate, by way of examples and not limitation, some systems to stochastically modulate neuromodulation implemented using a programming device and a neuromodulation device.
Figure 6B:
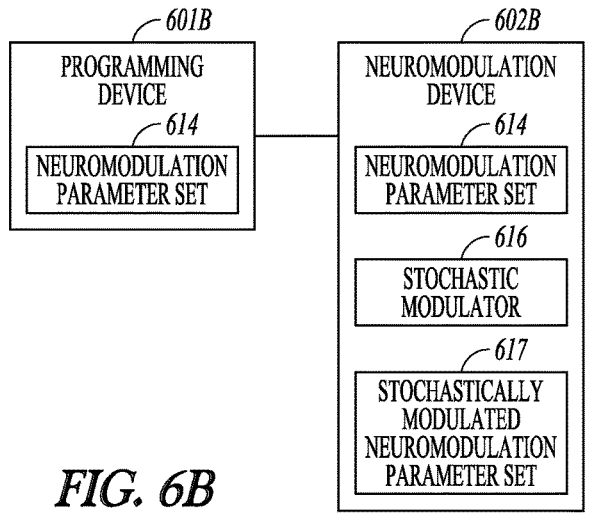

FIGS. 6A-6D illustrate, by way of examples and not limitation, some systems to stochastically modulate neuromodulation implemented using a programming device and a neuromodulation device. Each of the illustrated systems in FIGS. 6A-6D include a programming device and a neuromodulation device configured to communicate with each other, and the systems further include a stochastic modulator 616 to provide the stochastically-modulated neuromodulation parameter set 617 from the neuromodulation parameter set 614. In FIG. 6A, for example, the programming device 601A may include the neuromodulation parameter set 614 and the stochastic modulator 616 which may be used to modulate at least one parameter within the neuromodulator parameter set 614 to form the stochastically-modulated neuromodulation parameter set 617. The programming device 601A may program the stochastically-modulated neuromodulation parameter set 617 into the neuromodulation device 602A. In FIG. 6B, for example, the programming device 601B may program the neuromodulation parameter set into the neuromodulation device 602B. The neuromodulation device 602B may include the stochastic modulator 616 which may be used to modulate at least one parameter within the neuromodulator parameter set 614 to form the stochastically-modulated neuromodulation parameter set 617. The stochastically-modulated neuromodulation parameter set 617 may be stored in a non-volatile or persistent memory, or may be generated in real time or near real time by the neuromodulation device 602B as needed to generate the stochastically-modulated neuromodulation field.

Figure 6C:
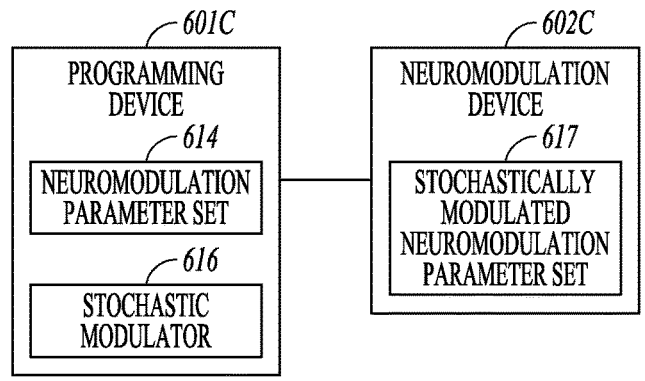

In FIG. 6C, for example, the programming device 601C may include the neuromodulation parameter set 614 and the stochastic modulator 616 which may be used to modulate at least one parameter within the neuromodulator parameter set 614 to program the stochastically-modulated neuromodulation parameter set 617 into the neuromodulation device 602C, which may be done without persistently storing the stochastically-modulated neuromodulation parameter set 617 in the programming device 601C. Rather, the programming device 601C may program the neuromodulation device 602C in real or near real time as it modulates the neuromodulation parameter set 614 into the stochastically-modulated neuromodulation parameter set 617.

Figure 6D:
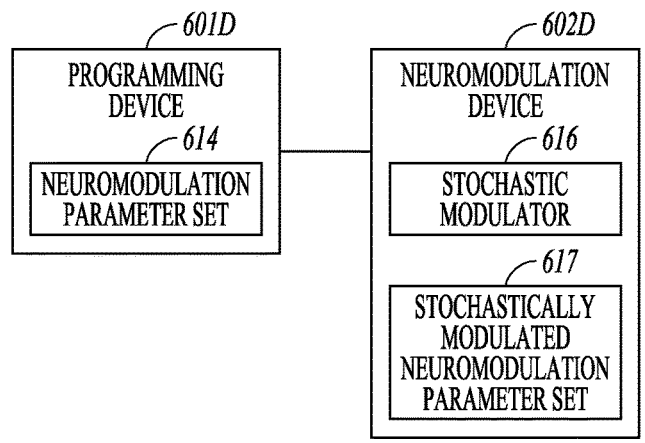

In FIG. 6D, for example, the programming device 601D may be programmed with the neuromodulation parameter set 614. The neuromodulation device 602D may include the stochastic modulator 616 which may be used to access the neuromodulator parameter set 614 in the programming device 601B and modulate at least one parameter within the neuromodulator parameter set 614 to form the stochastically-modulated neuromodulation parameter set 617. The stochastically-modulated neuromodulation parameter set 617 may be stored in a non-volatile or persistent memory, or may be generated in real time or near real time as needed to generate the stochastically-modulated modulation field.

Figure 7:
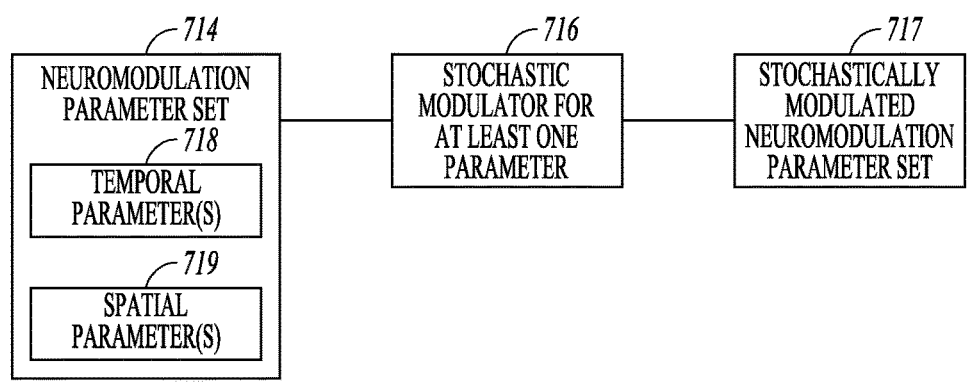
FIG. 7 illustrates, by way of example and not limitation, a system to stochastically modulate temporal and/or spatial neuromodulation parameters.

FIG. 7 illustrates, by way of example and not limitation, a system to stochastically modulate temporal and/or spatial neuromodulation parameters. The illustrated system may include at least one neuromodulation parameter set 714 that includes a plurality of parameters that maybe used to define the neuromodulation pulse parameters (e.g. amplitude, pulse width, pulse frequency, etc.) and electrode configuration(s) used in the neuromodulation. The at least one neuromodulation parameter set may include one or more temporal parameters selected to be stochastically-modulated by a stochastic modulator 716 to provide a stochastically-modulated neuromodulation parameter set 717 and/or may include one or more spatial parameter(s) selected to be stochastically-modulated by a stochastic modulator 716 to provide a stochastically-modulated neuromodulation parameter set 717. The stochastically-modulated neuromodulation parameter set 717 may be used to generate the stochastically-modulated neuromodulation field.

Figure 8:
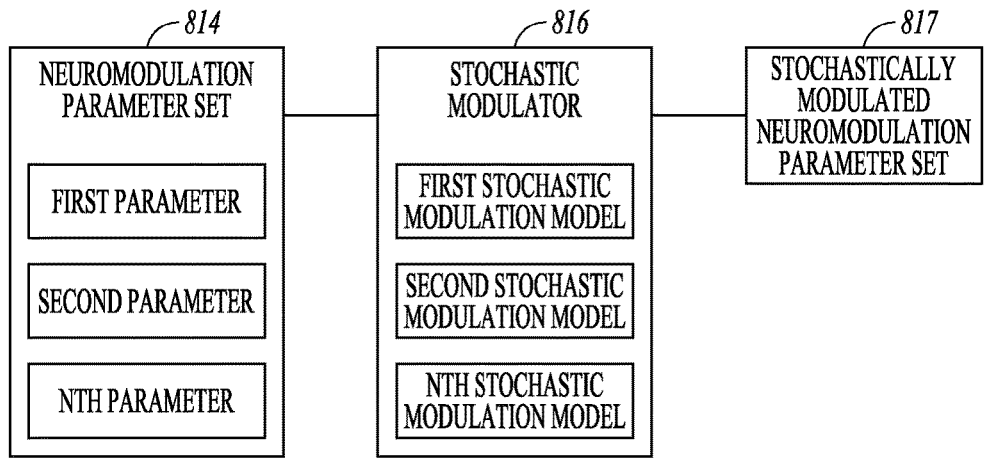
FIG. 8 illustrates, by way of example and not limitation, a system to stochastically modulate one or more neuromodulation parameter(s) using one or more stochastic modulation model(s).

FIG. 8 illustrates, by way of example and not limitation, a system to stochastically modulate one or more neuromodulation parameters using one or more stochastic modulation models (e.g. probabilistic distribution model or stochastic process model or real-time/semi-real-time computational model). Similar to FIG. 5, the illustrated system may include at least one neuromodulation parameter set 814 that includes a plurality of parameters that maybe used to define the neuromodulation pulse parameters (e.g. amplitude, pulse width, pulse frequency, etc) and electrode configuration(s) used in the neuromodulation. The at least one neuromodulation parameter set may include one or more neuromodulation parameters 815 selected to be stochastically-modulated by a stochastic modulator 816 to provide a stochastically-modulated neuromodulation parameter set 817. The stochastic modulator 816 may be programmed with one or more modulation model(s) (e.g. probabilistic distribution model(s) or stochastic process model(s) or real-time/semi-real-time computational model(s). In some embodiments, the system may be configured to allow a user to select the distribution to be used to stochastically modulate parameter(s) and/or to select a parameter(s) to be stochastically modulated. Each probabilistic distribution may be used to stochastically modulate one or more parameters in the neuromodulation parameter set. By way of example, a first probabilistic distribution may be used to stochastically modulate a first parameter, a second probabilistic distribution may be used to stochastically modulate a second parameter, and an nth probabilistic distribution may be used to stochastically modulate an nth parameter. The probabilistic distributions may be known distributions, such as Poisson or Gaussian by way of example and not limitation, that may be used to model neural tissue or may be developed to model targeted neural activity. The present subject matter is not limited to known probability distributions or stochastic processes. Additionally or alternatively to known probability distributions or stochastic processes, the model(s) used for the stochastic modulation can be a computation simulation or a/semi-real-time computational modeling based on neural recording.

Figure 9:
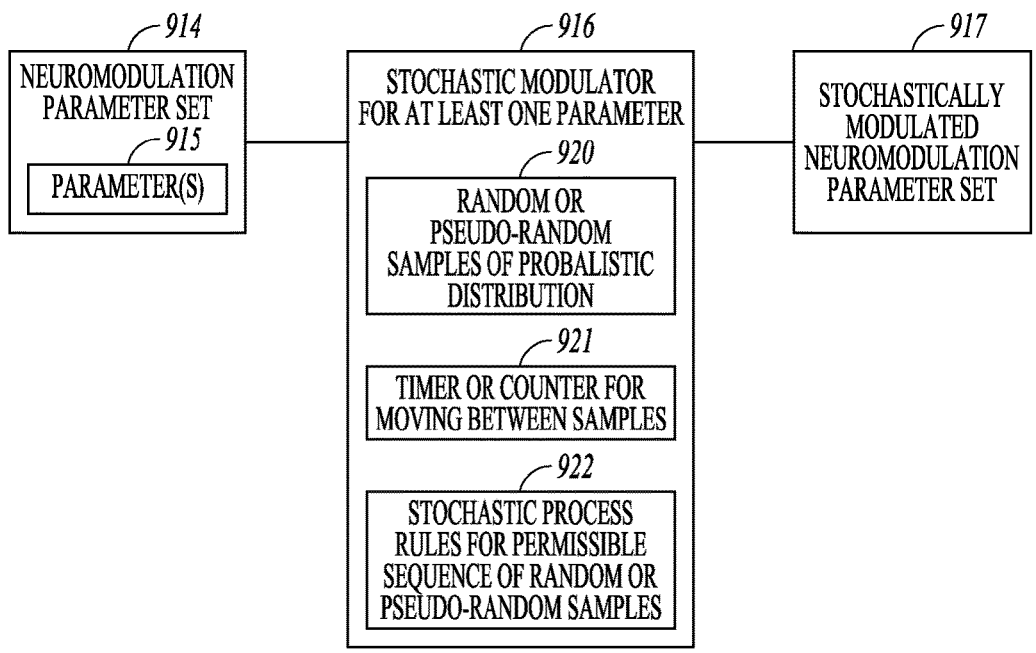
FIG. 9 illustrates, by way of examples and not limitation, some features that may be implemented in various stochastic modulator embodiments.

FIG. 9 illustrates, by way of examples and not limitation, some features that may be implemented in various stochastic modulator embodiments. Similar to FIG. 5, the illustrated system may include at least one neuromodulation parameter set 914 that includes a plurality of parameters that maybe used to define the neuromodulation pulse parameters (e.g. amplitude, pulse width, pulse frequency, etc) and electrode configuration(s) used in the neuromodulation. The at least one neuromodulation parameter set may include one or more neuromodulation parameters 915 selected to be stochastically-modulated by a stochastic modulator 916 to provide a stochastically-modulated neuromodulation parameter set 917.

As generally illustrated at 920, the stochastic modulator 916 may be configured to use random or pseudo-random samples of the probability distribution or stochastic process to stochastically modulate the at least one parameter. The stochastic modulator 916 may be configured with a timer or a counter 921 for moving between samples. For example, one sample may be used to modulate one pulse before advancing to another sample to modulate a subsequent pulse, or one sample may be used to modulate multiple pulses before advancing to another sample to modulate subsequent pulses. The stochastic modulator 916 may be configured with stochastic process rules, as generally illustrated at 922, used to identify if a subsequent sample is permissible for a sequence of random or pseudo-random samples used to stochastically modulate the at least one parameter.

Figure 10:
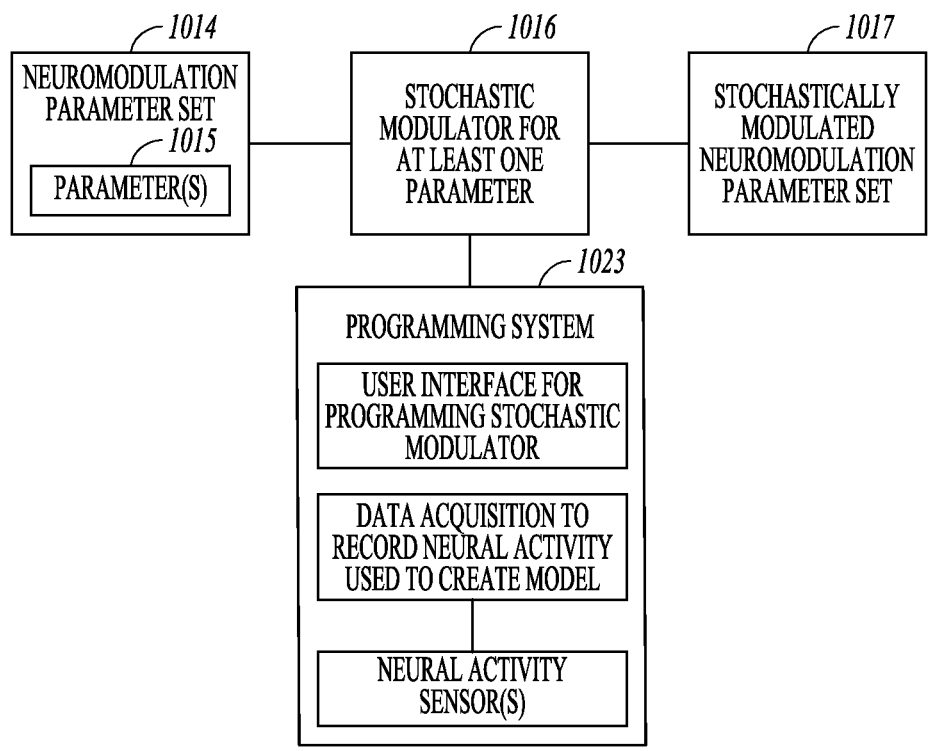
FIG. 10 illustrates, by way of example and not limitation, a system with a user interface used to program the stochastic modulator.

FIG. 10 illustrates, by way of example and not limitation, a system with a user interface used to program the stochastic modulator. Similar to FIG. 5, the illustrated system may include at least one neuromodulation parameter set 1014 that includes a plurality of parameters that maybe used to define the neuromodulation pulse parameters. One or more neuromodulation parameters 1015 selected to be stochastically-modulated by a stochastic modulator 1016 to provide a stochastically-modulated neuromodulation parameter set 1017. In the example illustrated in FIG. 10, the system includes a programming system 1023 configured for use to program the stochastic modulator 1016. The programming system 1023 may include a user interface, which may be part of a programming device or another external device accessible by a user. The user interface may be used to program a stochastic modulator in a programming device or a stochastic modulator in an implantable or external neuromodulation device. Some external neuromodulation devices may have a user interface. A non-exhaustive example of a user interface is provided in FIG. 11. The programming system may include neural activity sensor(s) and a data acquisition model to record neural activity. The neural data may be fed into the stochastic modulator for use in creating a real-time/semi-real-time computational model for modulation. Real-time/semi-real-time is understood to include near real-time for dynamically generating the model.

Figure 11:
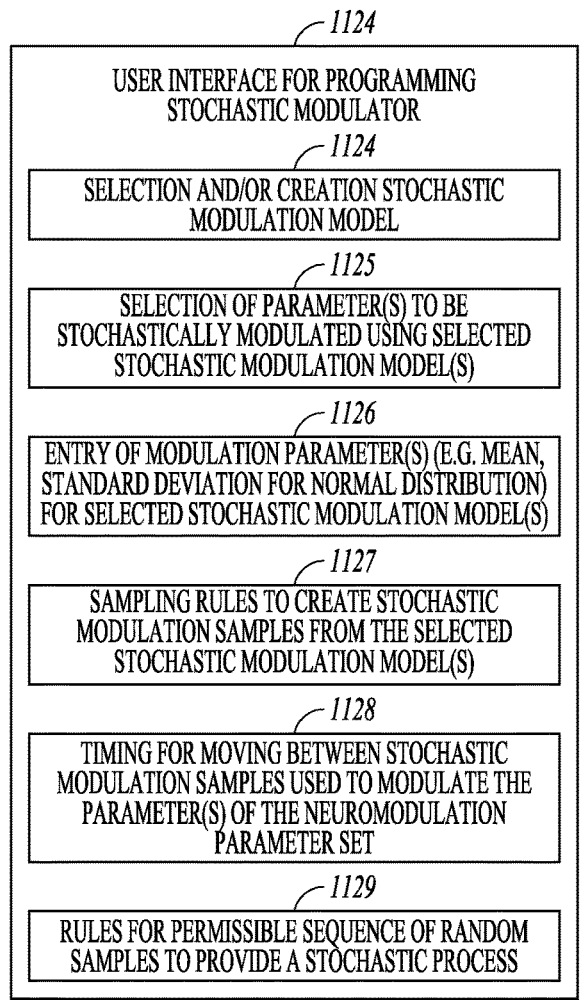
FIG. 11 illustrates, by way of examples and not limitation, some features that may be implemented in the user interface.

FIG. 11 illustrates, by way of examples and not limitation, some features that may be implemented in the user interface. The user interface 1123 illustrates example(s) of the user interface 1023 illustrated in FIG. 10. Various embodiments of the user interface 1123 may include any one of the illustrated features and may include any combination of two or more of the illustrated features. The user interface 1123 may include a feature to enable a user-selection of stochastic modulation model(s) 1124 to be used by the stochastic modulator. The user interface 1123 may include a feature to enable a user-selection of neuromodulation parameter(s) 1125 to be stochastically-modulated using stochastic modulation model(s). By way of example, the parameter(s) may include temporal neuromodulation parameters that control the timing of the neuromodulation pulses (e.g. frequency, pulse width, start/stop times, etc.), or may include spatial neuromodulation parameter(s) that control the location and shape of the neuromodulation field.

The user interface 1123 may include a feature to enable a user to select or enter modulation parameter(s) that at least partially define the stochastic modulation model(s) 1126. In some embodiments, stochastic modulation models may include a Poisson distribution or a normal distribution. By way of example and not limitation, lambda may be considered a modulation parameter for a Poisson distribution, and mean and standard deviation may be considered modulation parameters for a normal distribution. Further, by way of example, if a user selects pulse frequency as the parameter to be stochastically-modulated, the user can also select the mean value for the frequency to control the average therapeutic dose delivered to the targeted neural tissue. Selection of a relatively smaller standard deviation provides more randomized or pseudo-randomized samples that are closer to the mean, and selection of a relatively large standard deviation provides more randomized or pseudo-randomized samples that are further away from the mean. The system may be designed to provide pre-set or user-programmable safety limits. The safety limits may be incorporated using, by way of example, hardware or firmware or software, and may be configured to limit the average charge or charge density or may limit the average charge per phase or charge density per phase. In a normal distribution, for example, some embodiments may allow the user to enter a sigma value to prohibit the extremes in the distribution. A value of 2 sigma, by way of example, may be used prohibit about the lowest 2% and the highest 2% in the normal distribution from being used to stochastically modulate the neuromodulation parameter (or allow about the 95% in the middle of the normal distribution to stochastically modulate the neuromodulation parameter). In various embodiments, the modulation parameter(s) that can be entered or selected by the user may also include sigma values or other values to restrict the permissible range of random values in the probabilistic distribution.

The user interface 1123 may include a feature to enable a user to select or enter sampling rules 1127 to create stochastic modulation samples from stochastic modulation model(s). Thus, rather than randomize all available values in the stochastic modulation model (e.g. probabilistic distribution), some embodiments may use a sampling technique to provide a smaller subset of stochastic modulation samples that is representative of the model (e.g. probabilistic distribution) that can be used to stochastically modulate the neuromodulation parameter(s). The user interface 1123 may include a feature to control the timing 1128 for moving between stochastic modulation samples. For example, one sample may be used to modulate one pulse before advancing to another sample to modulate a subsequent pulse, or one sample may be used to modulate multiple pulses before advancing to another sample to modulate subsequent pulses.

The user interface 1123 may include a feature to enable a user to select or enter stochastic process rules 1129 that control or identify if subsequent sample(s) is (are) permissible in a sequence of random or pseudo-random samples. Thus, by way of example, the system is able to avoid extreme changes or jumps in the values within the probabilistic distribution and thus mimic naturally-occurring neuronal activity processed by the central nervous system.

Figure 12:
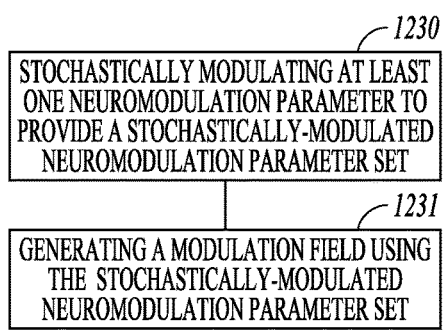
FIG. 12 illustrates, by way of example and not limitation, a method for delivering stochastic neuromodulation.

FIG. 12 illustrates, by way of example and not limitation, a method for delivering stochastic neuromodulation. The illustrated method may be performed using a variety of neuromodulation devices delivering a variety of neuromodulation therapies. By way of example and not limitation, the method may be performed to deliver neural stimulation to neural tissue in and around the spine, in the brain, and in peripheral nerves such as but not limited to the vagus nerve, the carotid sinus nerve, the renal nerve, etc., and may be performed to provide functional modulation such as may be implemented for physical therapy or to improve cognitive function. In the illustrated method for delivering neuromodulation, at least one neuromodulation parameter is stochastically-modulated to provide a stochastically-modulated neuromodulation parameter set 1230. A neuromodulation field is generated using the stochastically-modulated neuromodulation parameter set 1231. As described herein, a probabilistic distribution may be used to stochastically modulate the at least one parameter to provide the at least one stochastically-modulated parameter. Another probabilistic distribution may be used to stochastically-modulate at least one other parameter. In some embodiments, stochastic process rules may be implemented to enforce a permissible sequence of random or pseudo-random samples of a probabilistic distribution used to stochastically modulate the parameter(s). In some embodiments, the stochastically-modulated neuromodulation parameter(s) include a temporal neuromodulation parameter. In some embodiments, the stochastically-modulated neuromodulation parameter(s) include a spatial neuromodulation parameter.

Various embodiments are illustrated in the figures above. One or more features from one or more of these embodiments may be combined to form other embodiments. By way of examples and not limitation, one or more features of the stochastic modulator illustrated in FIG. 9 may be incorporated into other stochastic modulators, and one or more features of the user interface illustrated in FIG. 11 may be incorporated into the systems illustrated in other figures.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for use with an electrode arrangement, comprising:
   a neuromodulation device configured to use electrodes in the electrode arrangement to generate a neuromodulation field, the neuromodulation device including a neuromodulation generator, a neuromodulation control circuit and a storage, the storage including a stochastically-modulated neuromodulation parameter set, the stochastically-modulated neuromodulation parameter set including at least one stochastically-modulated parameter, wherein the controller configured to control the neuromodulation generator using the stochastically-modulation parameter set to generate the neuromodulation field; and
   a stochastic modulator programmed with at least one modulation model for use to stochastically modulate at least one parameter to provide the at least one stochastically-modulated parameter, wherein the stochastic modulator is configured to:
      implement stochastic process rules to determine permissible subsequent samples in a sequence of random or pseudo-random samples from the at least one modulation model; and
      use the sequence of random or pseudo-random samples with the permissible subsequent samples to stochastically modulate the at least one parameter.

2. The system of claim 1, wherein the neuromodulation device includes the stochastic modulator.

3. The system of claim 1, wherein the system includes a programming device, wherein the programming device includes the stochastic modulator and is configured to program the stochastically-modulated neuromodulation parameter set into the neuromodulation device.

4. The system of claim 1, wherein the stochastic modulator is programmed with at least one of a probabilistic distribution model, or a stochastic process model, or a real-time/semi-real-time computational model.

5. The system of claim 4, wherein the stochastic modulator is programmed with another modulation model, and is configured to use the other modulation model to stochastically modulate another parameter.

6. The system of claim 1, wherein the stochastic modulator includes a timer or counter configured to control when the stochastic modulator advances from one sample to another sample.

7. The system of claim 1, further including a user interface configured for use to program the stochastic modulator.

8. The system of claim 7, wherein the user interface is configured to allow a user to select a modulation model to be used by the stochastic modulator.

9. The system of claim 7, wherein the user interface is configured to allow a user to select a parameter to be stochastically-modulated using the stochastic modulator.

10. The system of claim 7, wherein the user interface is configured to allow a user to select at least one model parameter for a stochastic modulation model, the at least one model parameter to at least partially define or constrain the stochastic modulation model.

11. The system of claim 1, wherein the at least one stochastically-modulated parameter includes a temporal modulation parameter.

12. The system of claim 1, wherein the at least one stochastically-modulated parameter includes a spatial parameter.

13. A method for delivering neuromodulation, comprising:
   stochastically modulating at least one neuromodulation parameter using at least one modulation model to provide a stochastically-modulated neuromodulation parameter set, wherein the stochastically modulating includes:
      implementing stochastic process rules to determine permissible subsequent samples in a sequence of random or pseudo-random samples from the at least one modulation model; and
      using the sequence of random or pseudo-random samples with the permissible subsequent samples to stochastically modulate the at least one neuromodulation parameter; and
   generating a neuromodulation field using the stochastically-modulated neuromodulation parameter set.

14. The method of claim 13, wherein the modulation model includes a probabilistic distribution model, or a stochastic process model, or a real-time/semi-real-time computational model.

15. The method of claim 13, further comprising using another modulation model to stochastically-modulate at least one other parameter.

16. The method of claim 13, wherein stochastically modulating at least one neuromodulation parameter includes stochastically modulating at least one temporal parameter or stochastically modulating at least one spatial parameter.

17. The system of claim 7, wherein the user interface is configured to allow a user to select sampling rules to create the random or pseudo-random samples of the stochastic modulation model.

18. The system of claim 7, wherein the user interface is configured to allow a user to select rules to control when the stochastic modulator advances from one sample to another sample.

19. The system of claim 7, wherein the user interface is configured to allow a user to select the stochastic process rules.

20. A non-transitory machine-readable medium including instructions, which when executed by a machine, cause the machine to:
   stochastically modulate at least one neuromodulation parameter using at least one modulation model to provide a stochastically-modulated neuromodulation parameter set, including:

implement stochastic process rules to determine permissible subsequent samples in a sequence of random or pseudo-random samples from the at least one modulation model; and use the sequence of random or pseudo-random samples with the permissible subsequent samples to stochastically modulate the at least one neuromodulation parameter; and generate a neuromodulation field using the stochastically-modulated neuromodulation parameter set.

* * * * *